US00PP16066P2

(12) United States Plant Patent
Bergman

(10) Patent No.: US PP16,066 P2
(45) Date of Patent: Oct. 25, 2005

(54) ***HIBISCUS* PLANT NAMED 'CASHMERE WIND'**

(50) Latin Name: *Hibiscus rosa-sinensis*
Varietal Denomination: Cashmere Wind

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 61 days.

(21) Appl. No.: 10/932,277

(22) Filed: Sep. 1, 2004

(51) Int. Cl.[7] ..... A01H 5/00
(52) U.S. Cl. ..... Plt./257
(58) Field of Search ..... Plt./257

*Primary Examiner*—Kent Bell
(74) *Attorney, Agent, or Firm*—C. A. Whealy

(57) ABSTRACT

A new and distinct *Hibiscus* plant named 'Cashmere Wind', characterized by its compact, upright, somewhat outwardly spreading, uniform, dense and symmetrical plant habit that is appropriate for container production; glossy dark green-colored leaves; uniform flowering habit; light golden yellow-colored flowers with a faint red-colored "star" in the flower throat; good resistance to flower bud abscission during shipping; and tolerance to pathogens common to *Hibiscus* grown under Florida production conditions.

2 Drawing Sheets

Botanical classification/cultivar designation: *Hibiscus rosa-sinensis* cultivar Cashmere Wind.

BACKGROUND OF THE INVENTION

The present invention relates to a new and distinct cultivar of *Hibiscus*, botanically known as *Hibiscus rosa-sinensis*, and hereinafter referred to by the name 'Cashmere Wind'.

The new *Hibiscus* is a product of a planned breeding program conducted by the Inventor in Alva, Fla. The objective of the breeding program is to create new freely-branching *Hibiscus* cultivars with a dense, uniform and compact plant habit appropriate for container production, early and uniform flowering, numerous flowers per lateral branch, desirable flower color and good postproduction longevity.

The new *Hibiscus* originated from a cross-pollination made by the Inventor in Alva, Fla. in early 1996, of a proprietary *Hibiscus rosa-sinensis* selection, designated as code number YB-1544, not patented, as the female, or seed, parent with a proprietary *Hibiscus rosa-sinensis* selection, designated as code number YB-1340, not patented, as the male, or pollen, parent. The cultivar Cashmere Wind was discovered and selected by the Inventor as a flowering plant within the progeny of the stated cross-pollination in a controlled environment in Alva, Fla., on Sep. 28, 1998.

Asexual reproduction of the new *Hibiscus* by vegetative terminal cuttings in a controlled environment in Alva, Fla. since November, 1998, has shown that the unique features of this new *Hibiscus* are stable and reproduced true to type in successive generations.

SUMMARY OF THE INVENTION

The cultivar Cashmere Wind has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Cashmere Wind'. These characteristics in combination distinguish 'Cashmere Wind' as a new and distinct cultivar:

1. Compact, upright, somewhat outwardly spreading, uniform, dense and symmetrical plant habit that is appropriate for container production.
2. Glossy dark green-colored leaves.
3. Uniform flowering habit.
4. Light golden yellow-colored flowers with a faint red-colored "star" in the flower throat.
5. Good resistance to flower bud abscission during shipping.
6. Tolerant to pathogens common to *Hibiscus* grown under Florida production conditions.

Plants of the new *Hibiscus* can be compared to plants of the female parent, the proprietary *Hibiscus* selection code number YB-1544. Plants of the new *Hibiscus* differ from plants of the female parent selection in the following characteristics:

1. Plants of the new *Hibiscus* are more vigorous than plants of the female parent selection.
2. Plants of the new *Hibiscus* flower about four days later than plants of the female parent selection.
3. Plants of the new *Hibiscus* have larger flowers than plants of the female parent selection.
4. Plants of the new *Hibiscus* and the female parent selection differ in flower coloration as plants of the female parent selection have pink-colored flowers.

Plants of the new *Hibiscus* can be compared to plants of the male parent, the proprietary *Hibiscus* selection code number YB-1340. Plants of the new *Hibiscus* differ from plants of the male parent selection in the following characteristics:

1. Plants of the new *Hibiscus* are more vigorous than plants of the male parent selection.
2. Petals of plants of the new *Hibiscus* have somewhat ruffled margins whereas petals of plants of the male parent selection have non-ruffled margins.
3. Plants of the new *Hibiscus* have smaller flowers than plants of the male parent selection.

4. Plants of the new *Hibiscus* and the male parent selection differ in flower coloration as plants of the male parent selection have pink-colored flowers.

Plants of the new *Hibiscus* can be compared to plants of the *Hibiscus* cultivar Golden Wind, disclosed in U.S. Plant Pat. No. 11,978. In side-by-side comparisons conducted in Alva, Fla., plants of the new *Hibiscus* differed from plants of the cultivar Golden Wind in the following characteristics:

1. Plants of the new *Hibiscus* were not as vigorous than plants of the cultivar Golden Wind.
2. Plants of the new *Hibiscus* were more outwardly spreading than and not as upright as plants of the cultivar Golden Wind.
3. Flowers of plants of the new *Hibiscus* were softer golden yellow in color than flowers of plants of the cultivar Golden Wind. In addition flowers of plants of the new *Hibiscus* had a faint red-colored "star" in the flower throat whereas flowers of plants of the cultivar Golden Wind had a distinct orange-colored "eye".

BRIEF DESCRIPTION OF THE PHOTOGRAPHS

The accompanying colored photographs illustrate the overall appearance of the new *Hibiscus*, showing the colors as true as it is reasonably possible to obtain in colored reproductions of this type. Colors in the photographs may differ slightly from the color values cited in the detailed botanical description which accurately describe the colors of the new *Hibiscus*.

The photograph on the first sheet comprises a side perspective view of five typical flowering plants of 'Cashmere Wind' grown in a container.

The photograph on the second sheet comprises a close-up view of typical flowers and leaves of 'Cashmere Wind'.

DETAILED BOTANICAL DESCRIPTION

The photographs and following observations, measurements and values describe plants grown in Alva, Fla., with five plants per 15-cm container in polyethylene-covered greenhouses during the spring under conditions which closely approximate commercial production. During the production of the plants, day temperatures ranged from 13 to 37° C. and night temperatures ranged from 13 to 26° C. Plants were about four months old when the photographs and the description were taken. In the description, color references are made to The Royal Horticultural Society Colour Chart, 1995 Edition, except where general terms of ordinary dictionary significance are used.

Botanical classification: *Hibiscus rosa-sinensis* cultivar Cashmere Wind.

Parentage:

*Female or seed parent.*—Proprietary selection of *Hibiscus rosa-sinensis* designated as code number YB-1544, not patented.

*Male or pollen parent.*—Proprietary selection of *Hibiscus rosa-sinensis* designated as code number YB-1340, not patented.

Propagation:

*Type.*—By vegetative terminal cuttings.

*Time to initiate roots.*—About 10 days at temperatures of 24° C.

*Time to develop roots.*—About 28 days at temperatures of 24° C.

*Root description.*—Thick, fibrous; white in color.

*Rooting habit.*—Somewhat freely branching; moderately dense.

Plant description:

*Plant form and growth habit.*—Perennial, evergreen, upright, somewhat outwardly spreading, compact, uniform, dense and symmetrical plant habit. Moderately vigorous growth habit.

*Branching habit.*—Freely branching, usually about four lateral branches develop after removal of terminal apex.

*Plant height.*—About 22 cm.

*Plant diameter* (*area of spread*).—About 32 cm.

*Lateral branch description.*—Length: About 16 cm. Diameter: About 5 mm. Texture: Immature, smooth; mature, woody and rough. Color: Immature: Darker than 146A. Mature: Close to 197B to 197C.

*Foliage description.*—Arrangement: Alternate, single; numerous; symmetrical. Length: About 7.7 cm. Width: About 6.5 cm. Shape: Roughly ovate. Apex: Acute. Base: Cordate. Margin: Serrate to crenate. Aspect: Concave; apex reflexed. Texture, upper and lower surfaces: Glabrous; leathery. Luster, upper surface: Glossy. Luster, lower surface: Somewhat glossy. Venation pattern: Palmate. Color: Young foliage, upper surface: More green than 147A. Young foliage, lower surface: More green than 146A. Mature foliage, upper surface: Darker than 147A; venation, similar to lamina. Mature foliage, lower surface: Close to 147A; venation, close to 146A. Petiole: Length: About 2.1 cm. Diameter: About 3.5 mm. Texture, upper and lower surfaces: Pubescent. Color, upper and lower surfaces: More green than 146A.

Flower description:

*Flower arrangement.*—Flowers arranged singly at terminal leaf axils. Freely flowering with usually about two or three flower buds and/or open flowers per terminal apex. Flowers face mostly upright.

*Flower appearance.*—Rounded, light golden yellow-colored flowers with a faint red-colored "star" in the flower throat. Flowers are open for about one day. Flowers persistent.

*Natural flowering season.*—Usually spring and summer or during periods of warm weather.

*Flower diameter.*—About 12.5 cm.

*Flower length* (*height*).—About 8.5 cm.

*Flower bud* (*just before showing color*).—Resistance to abscission during shipping: Plants of the new *Hibiscus* have been observed to resist flower bud drop when stored in a closed box for 5 days at 13° C. Rate of opening: About one or two days depending on temperatures. Length: About 2.5 cm. Diameter: About 1.4 cm. Shape: Oblong. Color: Close to 147A.

*Petals.*—Arrangement: Corolla consists of five petals that are fused at base; petals imbricate. Length: About 6.5 cm. Width: At widest point, about 5 cm; at base, about 9 mm. Shape: Spatulate. Apex: Rounded. Base: Attenuate. Margin: Entire; somewhat ruffled. Texture: Upper surface: Smooth, glabrous, satiny. Lower surface: Glabrous; somewhat rugose. Color: When opening and fully opened, upper surface: Close to 15B. When opening and fully opened, lower surface: Close to 15D. Throat: Spots forming a "star", close to 44A.

*Sepals.*—Appearance: Five sepals fused into a tubular star-shaped calyx. Length: About 2.3 cm. Width:

About 1.1 cm. Shape: Lanceolate. Apex: Sharply acute. Margin: Entire. Texture, upper surface: Smooth; waxy. Texture, lower surface: Pubescent. Color: Upper surface: Close to 144A. Lower surface: 146A.

*Bracts.*—Appearance: About seven fused at base. Length: About 1.3 cm. Width: About 1.5 mm. Shape: Linear. Apex: Acute. Margin: Entire. Texture, upper surface: Smooth, glabrous. Texture, lower surface: Sparsely pubescent. Color, upper and lower surfaces: Close to 147A.

*Peduncles.*—Length: About 2.5 cm. Diameter: About 3 mm. Angle: Upright to slightly bent. Strength: Strong, flexible. Texture: Pubescent. Color: Close to 146A.

*Reproductive organs.*—Androecium: Stamen number: Numerous, about 62. Filament length: About 4 mm. Filament color: Towards the apex, 52A; towards the base, 15D. Anther shape: Reniform. Anther size: About 2 mm by 1 mm. Anther color: Close to 15D. Amount of pollen: Abundant. Pollen color: Close to 15A. Gynoecium: Pistil length: About 6.7 cm. Pistil diameter: Apex: About 2 mm. Base: About 5 mm. Style texture: Smooth, waxy. Style color: 15B to 15C. Stigma appearance: Five, rounded. Stigma diameter: About 2.25 mm. Stigma color: 17A. Ovary color: 151D.

*Seed/fruit.*—Seed and fruit production has not been observed.

Temperature tolerance: Plants of the new *Hibiscus* have been obseved to tolerate temperatures from 0 to 38° C.

Disease tolerance: Plants of the new *Hibiscus* grown under Florida production conditions have shown to be relatively tolerant to pathogens common to *Hibiscus* such as Pseudomonas, Pythium and Phytophthora. Plants of the new *Hibiscus* have not been observed to be tolerant to pests and other pathogens.

It is claimed:

1. A new and distinct *Hibiscus* plant named 'Cashmere Wind', as illustrated and described.

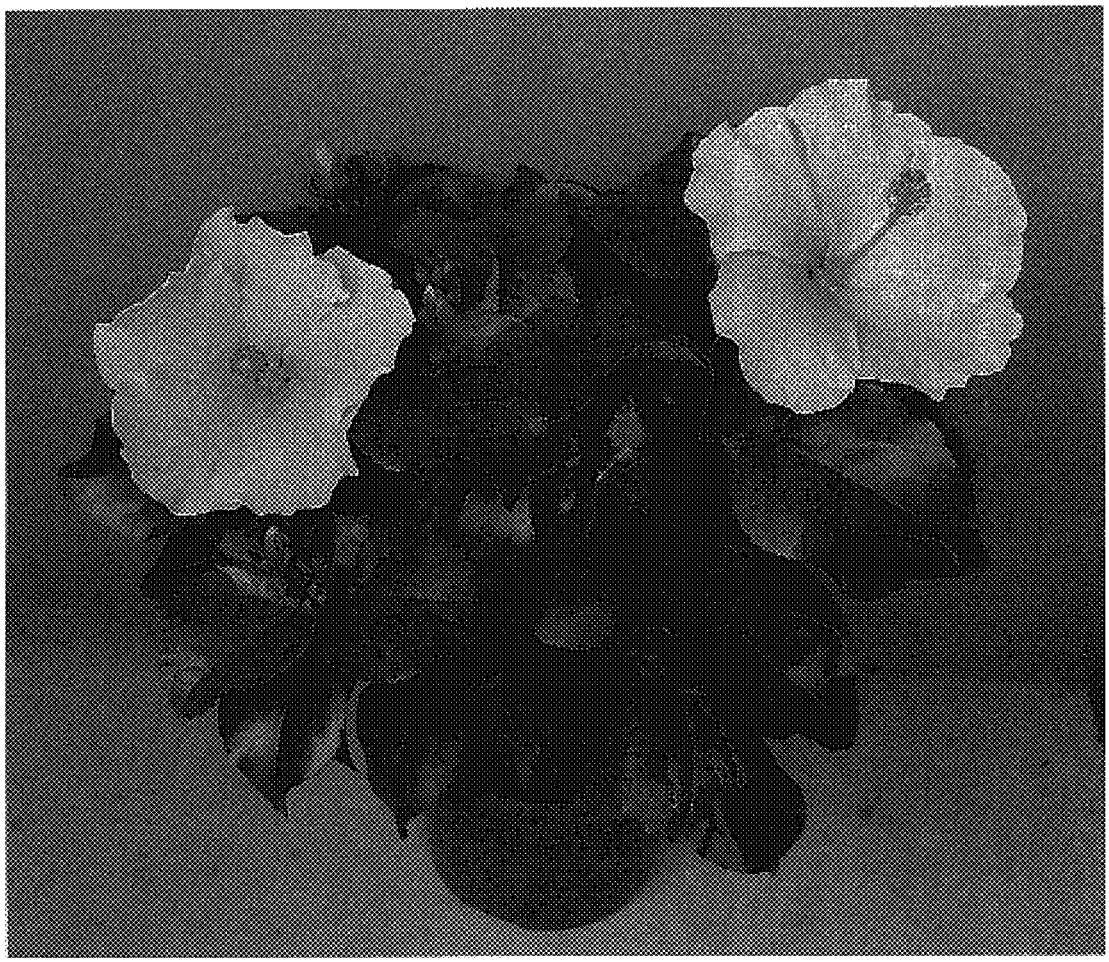

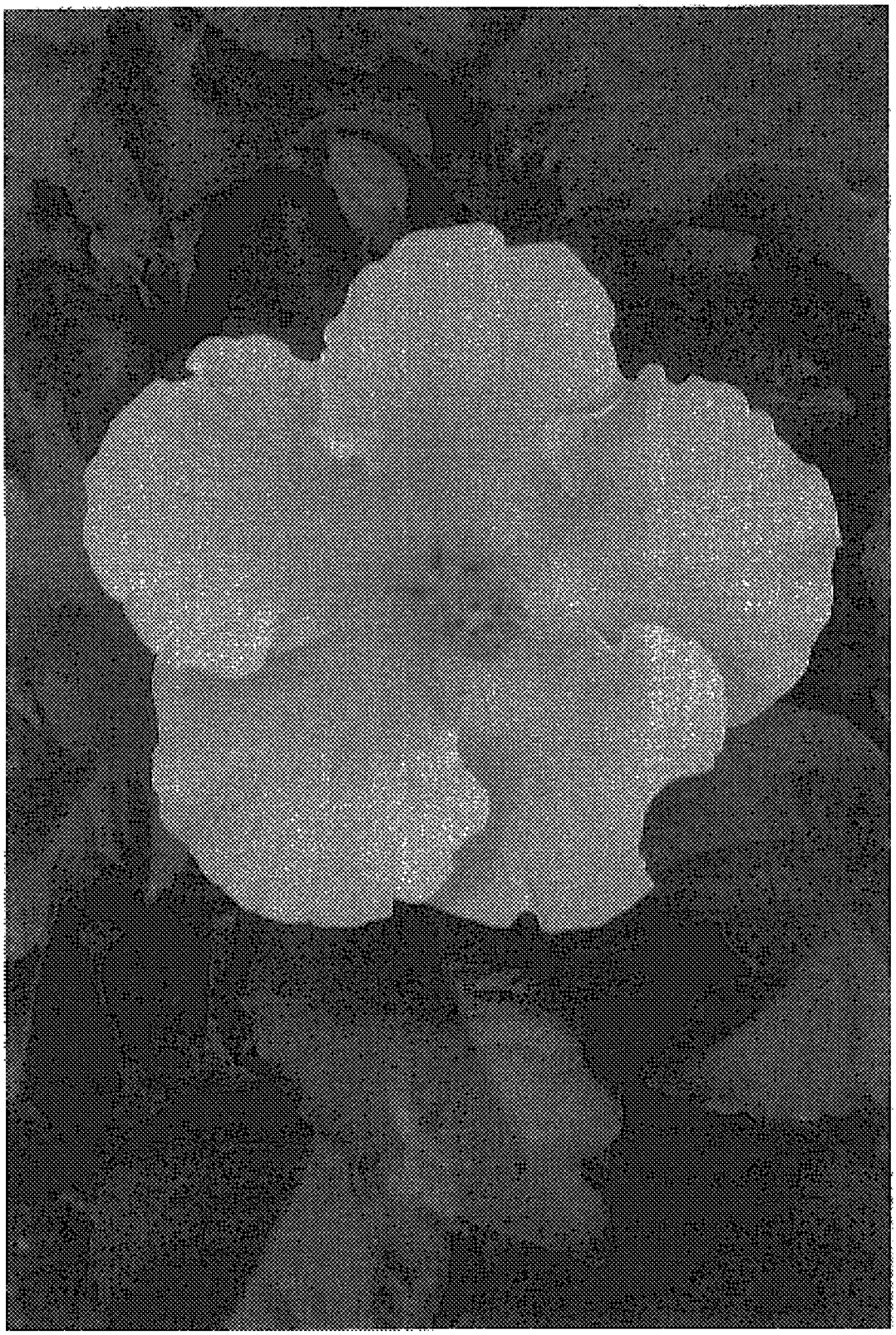

* * * * *